(12) United States Patent  (10) Patent No.: US 8,215,181 B1
Helmink  (45) Date of Patent: Jul. 10, 2012

(54) EVALUATION TECHNIQUE FOR BONDED, DUAL WALL STATIC AND ROTATING AIRFOIL MATERIALS

(75) Inventor: Randolph Clifford Helmink, Avon, IN (US)

(73) Assignee: Rolls-Royce North American Technologies, Inc., Indianapolis, IN (US)

( * ) Notice: Subject to any disclaimer, the term of this patent is extended or adjusted under 35 U.S.C. 154(b) by 349 days.

(21) Appl. No.: 12/553,209

(22) Filed: Sep. 3, 2009

Related U.S. Application Data

(60) Provisional application No. 61/190,965, filed on Sep. 4, 2008.

(51) Int. Cl.
*G01N 3/02* (2006.01)

(52) U.S. Cl. ............................................. 73/827; 73/760

(58) Field of Classification Search .................... 73/760, 73/827
See application file for complete search history.

(56) References Cited

U.S. PATENT DOCUMENTS

| | | | |
|---|---|---|---|
| 3,635,587 A * | 1/1972 | Giesman et al. ............ | 416/97 R |
| 4,334,495 A * | 6/1982 | Derkacs et al. .............. | 118/669 |
| 4,524,620 A * | 6/1985 | Wright et al. ................... | 73/587 |
| 4,841,124 A * | 6/1989 | Cox deceased et al. ...... | 219/201 |
| 5,113,583 A | 5/1992 | Jenkel et al. | |
| 5,269,058 A | 12/1993 | Wiggs et al. | |
| 5,273,708 A | 12/1993 | Freeman | |
| 5,469,618 A | 11/1995 | LeMonds et al. | |
| 5,503,532 A | 4/1996 | Schilling | |
| 5,626,462 A * | 5/1997 | Jackson et al. .............. | 416/97 R |
| 5,630,890 A | 5/1997 | Smashey et al. | |
| 5,640,767 A * | 6/1997 | Jackson et al. ........... | 29/889.721 |
| 5,753,053 A | 5/1998 | Smashey et al. | |
| 6,003,754 A | 12/1999 | Rhodes | |
| 6,003,756 A | 12/1999 | Rhodes | |
| 6,162,347 A | 12/2000 | Fleck | |
| 6,190,133 B1 | 2/2001 | Ress, Jr. et al. | |
| 6,638,639 B1 | 10/2003 | Burke et al. | |
| 6,935,187 B1 | 8/2005 | Gorman et al. | |
| 6,940,186 B2 * | 9/2005 | Weitkamp ....................... | 290/44 |
| 6,942,450 B2 * | 9/2005 | Yang et al. .................... | 415/115 |
| 7,448,433 B2 * | 11/2008 | Ortiz et al. .................... | 164/516 |
| 7,600,966 B2 * | 10/2009 | Devore et al. ................. | 415/115 |
| 7,695,245 B1 * | 4/2010 | Liang ................................ | 416/1 |
| 7,883,319 B2 * | 2/2011 | Volkmer ......................... | 416/61 |
| 7,970,555 B2 * | 6/2011 | Kernozicky et al. ............ | 702/34 |
| 2005/0193831 A1 | 9/2005 | Gorman et al. | |
| 2006/0260125 A1 | 11/2006 | Arnold et al. | |

* cited by examiner

*Primary Examiner* — Max Noori
(74) *Attorney, Agent, or Firm* — Krieg DeVault LLP

(57) ABSTRACT

The present invention provides a test specimen configured for mechanical load life characterization testing of a dual wall bonded airfoil for use in a turbomachinery device. The dual wall bonded airfoil has a spar and a skin bonded to the spar. The test specimen includes a main stress body, which includes a test spar component configured to represent the spar of the dual wall bonded airfoil; a test skin component configured to represent the skin of the dual wall bonded airfoil; and a test bond joint bonding the skin component to the spar component. The test bond joint is configured to represent the actual bond joint between the spar and the skin of the dual wall bonded airfoil. The test specimen is structured to simulate the dual wall bonded airfoil for testing in a mechanical testing machine.

15 Claims, 4 Drawing Sheets

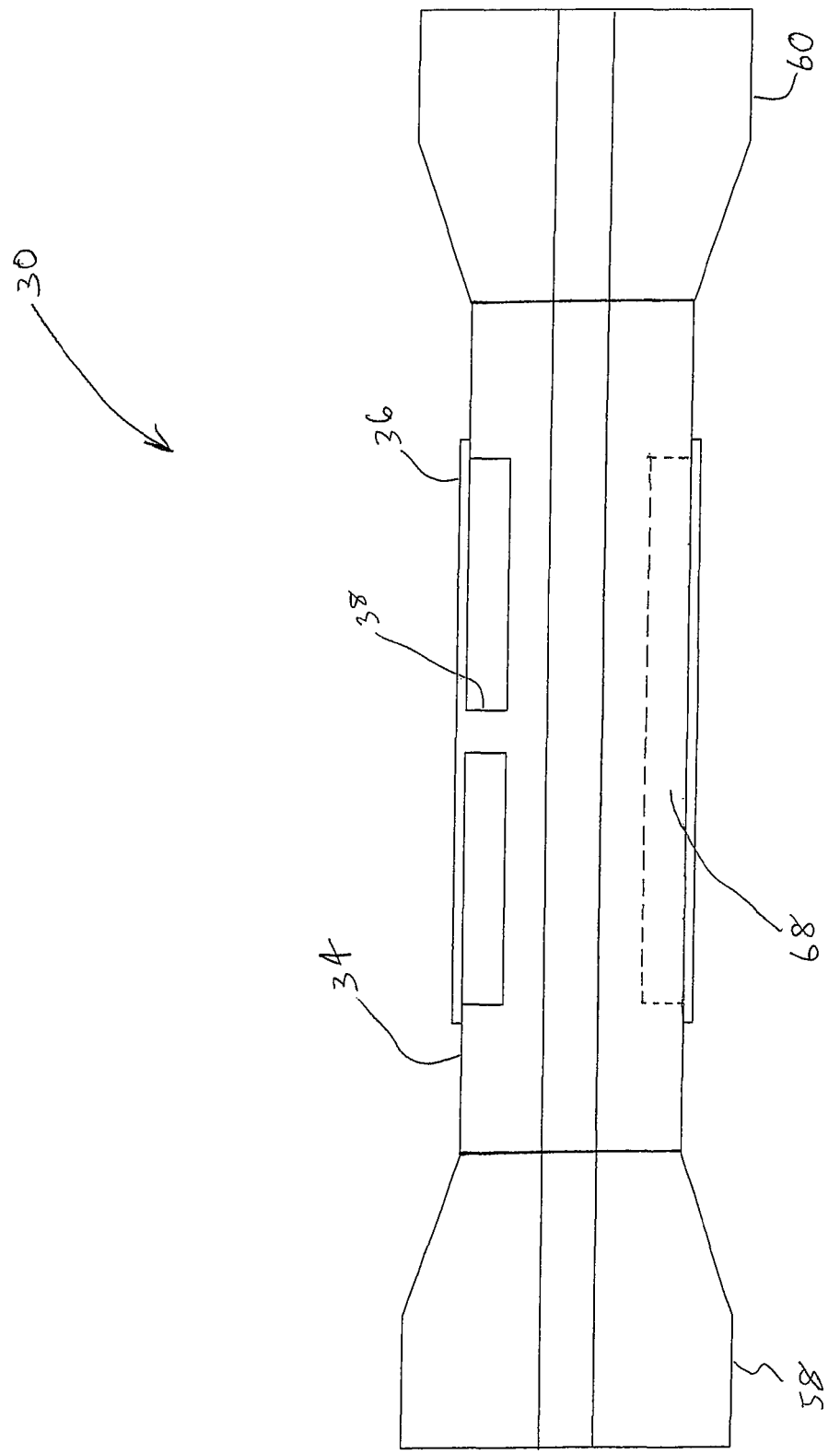

EVALUATION TECHNIQUE FOR BONDED, DUAL WALL STATIC AND ROTATING AIRFOIL MATERIALS

CROSS REFERENCE TO RELATED APPLICATIONS

The present application claims the benefit of U.S. Provisional Patent Application No. 61/190,965, filed Sep. 4, 2008, and is incorporated herein by reference.

FIELD OF THE INVENTION

The present invention relates to airfoils, and more particularly, to a test specimen configured for life characterization testing of a dual wall bonded airfoil.

BACKGROUND

Dual wall turbine blade and vane airfoils may be manufactured by bonding a skin to a spar. Typically, both the skin and spar are formed by casting, although different manufacturing techniques may be employed. For example, the spar may be machined from a bar stock, and the skin may be in the form of sheet meta, however other material configurations are contemplated herein. In any event, a number of material combinations may be proposed for use as the skin and spar materials for bonded dual wall airfoils, for example, turbine blade airfoils, and turbine vane airfoils. These materials may have a wide range of material characteristics and properties, which would affect the failure modes of the dual wall bonded airfoil and the materials' response to complex loading in service in a gas turbine engine. The complex configurations of dual wall bonded airfoils and the complex operating conditions in which such airfoils operate in the gas turbine make it difficult to determine the relative merits of the various material combinations analytically. It would be desirable to be able to test various combinations of materials for the spar and skin, as well as the bond joints where the skin is attached to the spar, in order to perform life characterization of such combinations under the mechanical and thermal-mechanical loading conditions anticipated in service in the engine. However, the loading on such airfoils is difficult and expensive to capture in test rigs, since such testing typically requires fabricating dual wall bonded airfoils from each of the material combinations, and then testing the airfoils in expensive custom-built test rigs that secure the airfoils to the rig, e.g., via a rotating turbine disk, and subject the airfoils to the mechanical and thermal loading conditions seen in the engine.

Accordingly, what is needed in the art is an effective way to test skin and spar material combinations and the bond joints therebetween in a manner that captures thermal, mechanical and/or thermal-mechanical loading.

SUMMARY

The present invention provides a test specimen that is configured to represent a dual wall bonded airfoil. The test specimen may include a spar component, a skin component and bond joints that are configured to represent the skin, spar and bond joints of the actual dual wall bonded airfoil. In some embodiments, the test specimen may include pedestal components that are configured to represent the attachment geometry for one or more of the bond joints where the skin is bonded to the spar in the actual dual wall bonded airfoil. Embodiments of the present invention may include cooling features, such as a cooling air supply passage, impingement cooling holes and/or film cooling holes that may be structured in shape, size, location, orientation and/or number to represent corresponding features in the actual dual wall bonded airfoil. The test specimen may also include input load attachment features on one or both ends for interface with conventional load testing machines, which may be used to transmit loads to the main stress body of the test specimen.

BRIEF DESCRIPTION OF THE DRAWINGS

The description herein makes reference to the accompanying drawings wherein like reference numerals refer to like parts throughout the several views, and wherein:

FIG. 4 is another cross sectional view of the test specimen of FIG. 2, illustrating a bonding rib in accordance with an embodiment of the present invention.

DETAILED DESCRIPTION

Figure 1:
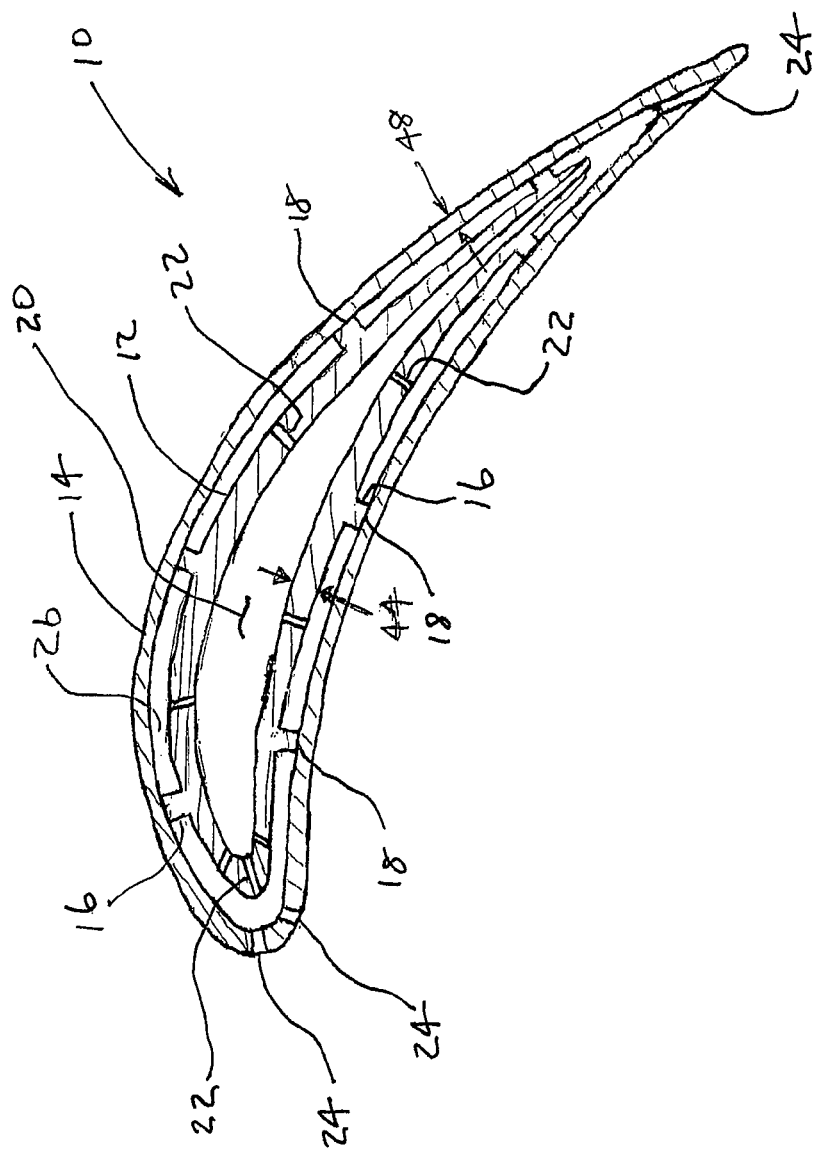
FIG. 1 generally depicts a cross section of a dual wall bonded airfoil.

For purposes of promoting an understanding of the principles of the invention, reference will now be made to the embodiments illustrated in the drawings, and specific language will be used to describe the same. It will nonetheless be understood that no limitation of the scope of the invention is intended by the illustration and description of certain embodiments of the invention. In addition, any alterations and/or modifications of the illustrated and/or described embodiment(s) are contemplated as being within the scope of the present invention. Further, any other applications of the principles of the invention, as illustrated and/or described herein, as would normally occur to one skilled in the art to which the invention pertains, are contemplated as being within the scope of the present invention.

Referring now to the drawings, and in particular, FIG. 1, a cross section of a dual wall bonded airfoil 10 is depicted, with respect to which an embodiment of the present invention is described. Although various features and components of dual wall bonded airfoil 10 are depicted in FIG. 1 and described herein, it will be understood that the presence of such features and components in the depicted and described embodiments are not limiting, and that other dual wall bonded airfoils having the same, different, less or more features may be employed without departing from the scope of the present invention. Dual wall bonded airfoil 10 may be an airfoil employed in a gas turbine engine, and may be, for example, a turbine blade or a turbine vane. Dual wall bonded airfoil 10 includes a spar 12 and a skin 14. A plurality of pedestals 16 extend between spar 12 and skin 14, which serve to space skin 14 apart from spar 12, and to support skin 14. In the depiction of FIG. 1, pedestals 16 are formed as part of spar 12, and extend outward toward skin 14. However, in other embodiments, pedestal 16 may be formed as part of skin 14, extending inward toward spar 12. Alternatively, a portion of pedestal 16 may be formed as part of spar 12, and another portion of pedestal 16 may be formed as part of skin 14. Pedestals 16 may vary in size and shape. In any event, dual wall bonded airfoil 10 includes a bond joint 18, such as a diffusion bond, which attaches skin 14 to spar 12, including at pedestals 16.

During the operations of the gas turbine engine in which dual wall bonded airfoil 10 is installed, that airfoil is exposed to various harsh conditions, including high operating temperatures, adverse temperature distributions, mechanical loading, and thermal mechanical loading resulting from the temperature conditions to which dual wall bonded airfoil 10 is exposed. Accordingly, dual wall bonded airfoil 10 may be a cooled airfoil.

For example, as depicted in FIG. 1, dual wall bonded airfoil 10 includes a cooling air supply passage 20, a plurality of impingement cooling holes 22, and a plurality of film cooling holes 24. Impingement cooling holes 22 are fluidly coupled to cooling air supply passage 20, and deliver cooling air into the cavity 26 formed between spar 12 and skin 14. Cooling air supply passage 20 provides cooling to spar 12. Impingement cooling holes 22 are configured in size, shape, location, orientation and number to impinge cooling air upon the internal surfaces of skin 14 in order to reduce the temperature of skin 14. Film cooling holes 24 are fluidly coupled to impingement cooling holes 22, e.g., via cavity 26, and are configured in size, shape, location, orientation, and number to provide film cooling for the surface of skin 14 of dual wall bonded airfoil 10.

During the operation of the gas turbine engine, the temperatures of spar 12 and skin 14 are sought to be maintained at temperatures that are suitable for the materials from which spar 12 and skin 14 are made and the stresses imposed on dual wall bonded airfoil 12. In order to confirm the capabilities of spar 12, skin 14 and bond joint 18 for purposes of life determination, it is desirable to test dual wall bonded airfoil 10 in conditions that simulate the operating conditions to which dual wall bonded airfoil 10 is exposed during normal operations of the gas turbine engine. However, doing so may be expensive, at least because of the manufacturing requirements associated with producing dual wall bonded airfoil 10, and because various different materials for spar 12 and skin 14 and different bond techniques and/or materials for bond joint 18 may be desired to be tested.

In addition, any such testing would require a testing facility that is capable of imparting the appropriate loads and temperatures to the actual dual wall bonded airfoil 10, which may be expensive to build and operate. Accordingly, embodiments of the present invention are directed to providing a test specimen that simulates dual wall bonded airfoil 10, including spar 12, skin 14, pedestal 16, bond joint 18, cooling air supply passage 20, impingement cooling holes 22, film cooling holes 24 and cavity 26, but which is readily produced, and readily tested by conventional testing machines. By having a test specimen that adequately represents the characteristics of dual wall bonded airfoil 10, but yet, is structured to operate in a conventional mechanical testing machine, such as a tensile testing machine, a fatigue testing machine, a tensile/compression testing machine, etc., the goal of testing various aspects and materials of dual wall bonded airfoil 10 may be achieved, but with a substantially reduced cost.

Figure 2:
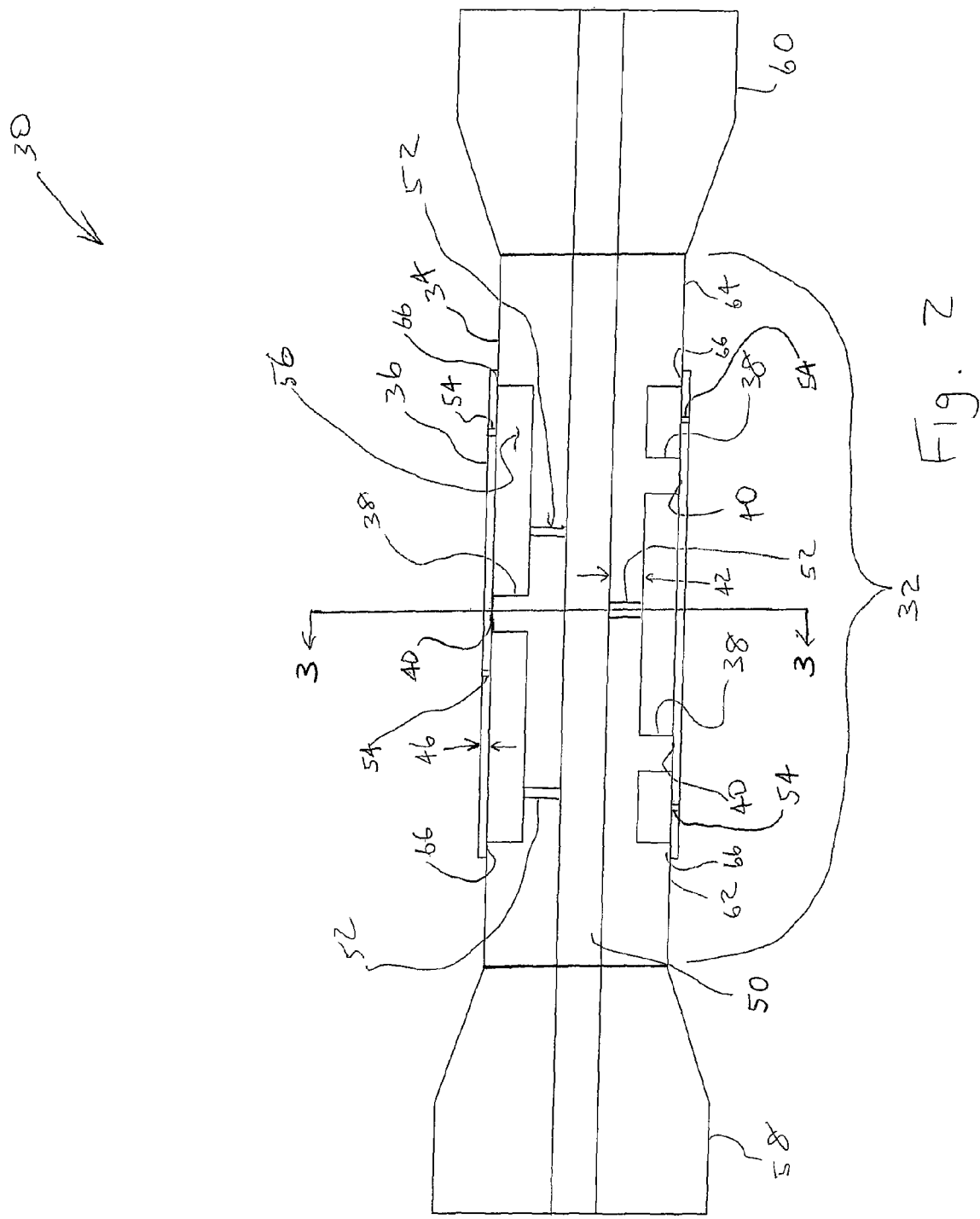
FIG. 2 depicts a lengthwise cross section of a generalized version of a test specimen in accordance with an embodiment of the present invention.

Referring to FIG. 2, a test specimen 30 configured for life characterization testing of a dual wall bonded airfoil for use in a turbomachinery device, such as a gas turbine engine, in accordance with an embodiment of the present invention is depicted. Although various features and components of test specimen are depicted in FIG. 2 and described herein, it will be understood that the presence of such features and components in the depicted and described embodiments are not limiting, and that other test specimens having the same, different, less or more features may be employed without departing from the scope of the present invention. Test specimen 30 includes a main test body 32, a test spar component 34, a test skin component 36, a plurality of test pedestal components 38 and test bond joints 40. Test spar component 34 is configured to represent spar 12 of dual wall bonded airfoil 10, and in the present embodiment is made from the same material as spar 12 of dual wall bonded airfoil 10. In the present embodiment, test spar component 34 is cylindrical, although it will be understood that other shapes may be employed without departing from the scope of the present invention.

Test skin component 36 is configured to represent the actual skin 14 of dual wall bonded airfoil 10, and in the present embodiment is made from the same material as the skin of dual wall bonded airfoil 10. Test pedestal component 38 is configured to represent the geometry of the actual pedestal 16 of dual wall bonded airfoil 10 where skin 14 of dual wall bonded airfoil 10 is bonded to spar 12. One or more of test pedestal components 38 extends between test spar component 34 and test skin component 36.

In the present embodiment, test pedestal components 38 are formed as part of test spar component 34, and extend outward toward test skin component 36. However, in other embodiments, test pedestal components 38 may be formed as part of test skin component 36, extending inward toward test spar component 34. Alternatively, a portion of a test pedestal component 38 may be formed as part of test spar component 34, and another portion may be formed as part of skin 14.

Test bond joint 40 bonds test skin component 36 to test spar component 34, and is configured to represent the actual bond joint 18 between spar 12 and skin 14 of dual wall bonded airfoil 10. In the present embodiment, test bond joint 40 is a diffusion bond, although it is alternatively contemplated that other types of bond joints may be employed without departing from the scope of the present invention.

Test specimen 30 is structured for testing in a mechanical testing machine to simulate dual wall bonded airfoil 10 for purposes of life characterization testing. In the present embodiment, test spar component 34 has a thickness 42, e.g., a cross-sectional thickness, corresponding to the thickness 44 of spar 12 at one or more locations, for example at such locations at which life characterization is sought. Similarly, in the present embodiment, test skin component 36 has a thickness 46 corresponding to the actual skin thickness 48 of skin 14 of dual wall bonded airfoil 10. It will be understood that other thicknesses for test spar component 34 and test skin component 36 may be employed without departing from the scope of the present invention.

In order to simulate the effects, e.g., stress risers and thermal gradients occurring due to the presence of cooling air supply passage 20, impingement cooling hole 22 and film cooling hole 24 of dual wall bonded airfoil 10, test specimen 30 may include test cooling features that are structured to represent the actual cooling features of dual wall bonded airfoil 10. For example, in the present embodiment, test cooling features include one or more of a test cooling air supply passage 50, a plurality of test impingement cooling holes 52 and a plurality of test film cooling holes 54. In the present embodiment, test impingement cooling holes 52 are fluidly coupled to test cooling air supply passage 50, although in other embodiments, other sources of cooling air may be employed without departing from the scope of the present invention. Also, in the present embodiment, test film cooling holes 54 are fluidly coupled to test impingement cooling hole 52 via a test cavity 56, although other sources of cooling air may be employed without departing from the scope of the present invention.

In the embodiment of FIG. 2, test impingement cooling holes 52 are formed in test spar component 34, and are configured to represent actual impingement cooling holes 22 in spar 12 of dual wall bonded airfoil 10. Test impingement cooling holes 52 are configured to impinge a cooling fluid, e.g., air, on test skin component 36. Test film cooling holes 54 are formed in test skin component 36, and are configured to represent actual film cooling holes 24 in skin 14 of dual wall bonded airfoil 10. Test film cooling holes 54 are configured to discharge the cooling fluid from test skin component 36.

Each of test cooling air supply passage 50, test impingement cooling holes 52 and test film cooling holes 54 are configured in size, shape, location, orientation and number to represent the respective cooling air supply passage 20, impingement cooling hole 22 and film cooling hole 24. However, it will be understood that the geometric parameters, e.g., size, shape, location, orientation and number, of test cooling air supply passage 50, test impingement cooling holes 52 and test film cooling holes 54 may vary from the present embodiment without departing from the scope of the present invention.

Test pedestal components 38 are configured in height to correspond to actual pedestals 16, e.g., so that test cavity 56 corresponds to actual cavity 26 of dual wall bonded airfoil 10, so that test skin component 36 is spaced apart from test spar component 34 to the same extent that skin 14 is spaced apart from spar 12. Although in the present embodiment, the various features and components of test specimen 30 are configured in size, orientation and position that correspond to the actual features and components of dual wall bonded airfoil 10, it will be understood by those skilled in the art that other sizes, orientations and positions may be employed without departing from the scope of the present invention. For example, in some embodiments the geometry of the test specimen 30 features and components may be altered to account for the fact that test specimen 30 is generally cylindrical, where as dual wall bonded airfoil 10 is not.

In order to accommodate installation into a conventional mechanical testing machine, test specimen 30 includes an input load attachment feature 58 and an input load attachment feature 60. Each of input load attachment feature 58 and input load attachment feature 60 is structured to both interface with the mechanical load testing machine and to transmit mechanical loads from the mechanical load testing machine to main stress body 32. In the present embodiment, each of input load attachment feature 58 and input load attachment feature 60 are formed as part of test spar component 34. Alternatively, it is contemplated that input load attachment feature 58 and input load attachment feature 60 may be inertia welded to test spar component 34, or may be attached to test spar component 34 via other means, such as brazing or bonding. The ends of test skin component 36 are coupled to end portion 62 and end portion 64 of main stress body 32 via bond joints 66, which are, for example, diffusion bond joints.

Figure 3:
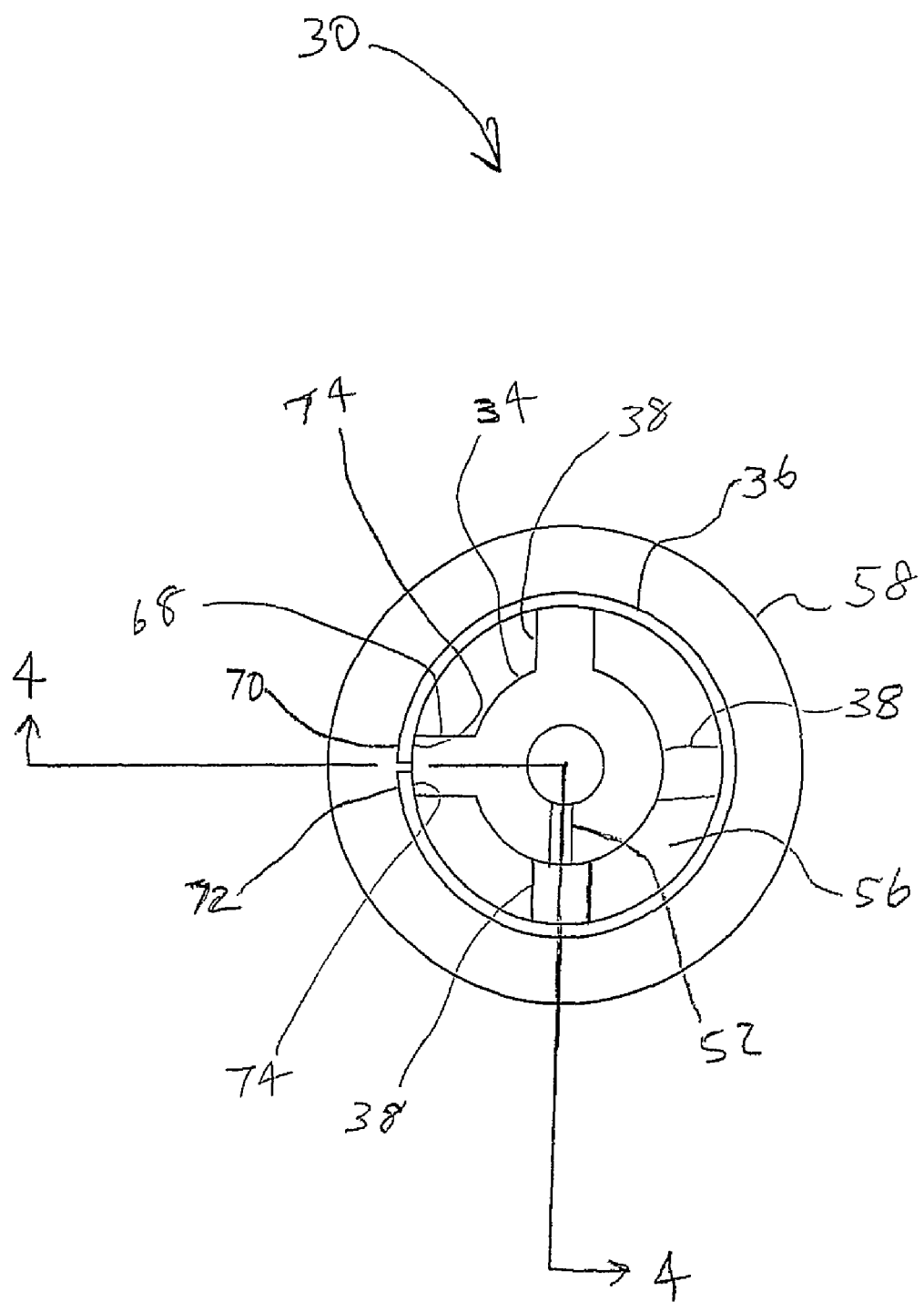
FIG. 3 is a cross sectional view taken at 90° from the view illustrated in FIG. 2.

Referring now to FIG. 3, a cross section of test specimen 30 is depicted. Test specimen 30 includes bonding rib 68 extending from test spar component 34 to interface with test skin component 36. Bonding rib 68 runs the length of main stress body 32. Test skin component 36 of the present embodiment is in the form of a sheet that is wrapped around test spar component 34 and meets at skin ends 70 and 72. Test skin component 36 is attached to bonding rib 68 along its length at bond joints 74, such as diffusion bond joints. Although the present embodiment has test skin component 36 in the form of a sheet that is wrapped around test spar component 34, it will be understood that in other embodiments, test skin component 36 may take the form of a hollow cylinder that is slid onto main stress body 32 prior to the attachment of input load attachment feature 58 and input load attachment feature 60.

Referring now to FIG. 4, a lengthwise cross sectional view of test specimen 30 is depicted, which illustrates bonding rib 68.

Test specimen 30 may be manufactured in various manners. For example, in one embodiment, test spar component 34 may be formed from a cylindrical bar of a candidate material envisioned for spar 12 of dual wall bonded airfoil 10. Starting with the cylindrical bar, test pedestal components 38 representing the attachment geometry between spar 12 and skin 14 of dual wall bonded airfoil 10 may be machined into the bar within a specified gauge length. As an alternative, test pedestal components 38 may be machined in a wax bar, or may be produced by wax injection, and a wax bar used to produce test spar component 34 in the form of a lost-wax investment casting of the desired geometry.

Test skin component 36 may be in the form of a sheet or a hollow cylinder of a candidate material envisioned for skin 14 of dual wall bonded airfoil 10. For test skin component 34 in the form of a sheet, the sheet may be a cast material, sheet metal, or a stamping, and may be wrapped around test spar component 34, leaving contain a small controlled gap between the axial edges of the sheet, and joined to test spar component 34 by diffusion brazing or a similar joining technique. For test skin component 34 in the form of a hollow cylindrical skin, test skin component 36 may be diffusion braised to test spar component 34 with test pedestal components 38 to produce the center section of the test specimen 30, i.e., main stress body 32.

The center of the bar may be removed by gun drilling to generate test cooling air supply passage 50. Test cooling air supply passage 50 may be produced before or after test skin component 36 is bonded to test spar component 34. End caps, e.g., input load attachment feature 58 and input load attachment feature 60 may be inertia welded to each end of the bimetallic main stress body 32 prior to gun drilling and finish machining. The net result is a test specimen 30 that may be finish machined and tested in a manner similar to conventional creep rupture, low cycle fatigue, high cycle fatigue and/or thermal-mechanical fatigue test specimens. Cooling air may be blown down the center, i.e., test cooling air supply passage 50, of test specimen 30 during the life characterization testing. Test impingement cooling holes 52 and test film cooling holes 54 may be formed in test spar component 34 and test skin component 36 to capture cooling air affects on thermal loading as well as capturing crack initiation at the stress concentrations represented by the holes as part of the life characterization of dual wall bonded airfoil 10.

Thus, in accordance with an embodiment of the present invention, test specimen 30 is structured to simulate dual wall bonded airfoil 10. Once produced, test specimen 30 may be subjected to mechanical testing using a conventional testing machine, after which the tested specimen 30 may be inspected for crack initiation, etc., in order to perform life characterization. In addition to mechanical testing, thermal mechanical testing may be performed by subjecting test specimen 30 to elevated temperatures in cyclic fashion using temperature profiles anticipated for dual wall bonded airfoil 10 in service, e.g., in a gas turbine engine. Such testing may include supplying cooling air at a temperature anticipated in service to test cooling air supply passage 50.

Thus, embodiments of the present invention may include a test specimen configured for mechanical load life characterization testing of a dual wall bonded airfoil for use in a turbomachinery device, such as a gas turbine engine, wherein the dual wall bonded airfoil has a spar and a skin bonded to the spar. The test specimen may include a main stress body. The main stress body may include a test spar component configured to represent the spar of the dual wall bonded airfoil; a test skin component configured to represent the skin of the dual wall bonded airfoil; and a test bond joint bonding the skin component to the spar component. The test skin component may have a skin thickness corresponding to the actual skin thickness of the skin of the dual wall bonded airfoil.

The test bond joint may be configured to represent the actual bond joint between the spar and the skin of the dual wall bonded airfoil, wherein the test specimen is structured to simulate the dual wall bonded airfoil for testing in a mechanical testing machine. The bond joint may be a diffusion bond joint.

The test specimen may also include one or more test pedestal components configured to represent a geometry of an actual pedestal of the dual wall bonded airfoil where the skin of the airfoil is bonded to the spar of the airfoil. The pedestal components may extend between the test spar component and the bond joint. In order to perform testing using a mechanical load testing machine, the test specimen may include first and second input load attachment features that are structured to both interface with the mechanical load testing machine and to transmit a mechanical load from the mechanical load testing machine to the main stress body.

The test spar component may be made from the same material as the spar of the dual wall bonded airfoil, and the test skin component may be made from the same material as the skin of the dual wall bonded airfoil.

The test specimen may also include one or more test cooling features structured to represent actual cooling features of the dual wall bonded airfoil. The test cooling feature may include a cooling supply channel formed in the test spar component, and also a test impingement cooling hole formed in the test spar component that is configured to represent an actual impingement cooling hole in the spar of the dual wall bonded airfoil. The test impingement cooling hole may be configured to impinge a cooling fluid on the test skin component. The test cooling feature may also include a test film cooling hole formed in the test skin component that is configured to represent an actual film cooling hole in the skin of the dual wall bonded airfoil. The test film cooling hole may be configured to discharge a cooling fluid from the test skin component.

In addition, embodiments of the present invention include a method of performing life characterization of a dual wall bonded airfoil for use in a turbomachinery device, the dual wall bonded airfoil having a spar and a skin bonded to the spar. The method may include forming a test specimen structured to simulate the dual wall bonded airfoil, including a test spar component, a test skin component and a test bond joint bonding the skin component to the spar component; performing mechanical testing of the test specimen using a mechanical testing machine; and inspecting the test specimen subsequent to performing the mechanical testing. The method may also include heating the test specimen during the mechanical testing, the heating being configured to represent thermal conditions seen by the dual wall bonded airfoil during the operation of the turbomachinery device. Also, the method may include providing cooling air internally to the test spar component during the mechanical testing.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A test specimen configured for mechanical load life characterization testing of a dual wall bonded airfoil for use in a turbomachinery device, the dual wall bonded airfoil having a spar and a skin bonded to the spar, the test specimen comprising:
    a main stress body, including:
    a test spar component configured to represent the spar of the dual wall bonded airfoil;
    a test skin component configured to represent the skin of the dual wall bonded airfoil; and
    a test bond joint bonding said skin component to said spar component, said test bond joint being configured to represent the actual bond joint between the spar and the skin of the dual wall bonded airfoil,
    wherein said test specimen is structured to simulate the dual wall bonded airfoil for testing in a mechanical testing machine.

2. The test specimen of claim 1, further comprising a test pedestal component configured to represent a geometry of an actual pedestal of the dual wall bonded airfoil where the skin of the airfoil is bonded to the spar of the airfoil.

3. The test specimen of claim 2, wherein said pedestal component extends between said test spar component and said bond joint.

4. The test specimen of claim 1, wherein the test bond joint is a diffusion bond joint.

5. The test specimen of claim 1, further comprising:
    a first input load attachment feature structured to both interface with the mechanical load testing machine and to transmit a mechanical load from the mechanical load testing machine to said main stress body; and
    a second input load attachment feature structured to both interface with the mechanical load testing machine and to transmit the mechanical load from the mechanical load testing machine to said main stress body.

6. The test specimen of claim 1, wherein said test spar component is made from the same material as the spar of the dual wall bonded airfoil.

7. The test specimen of claim 1, wherein said test skin component is made from the same material as the skin of the dual wall bonded airfoil.

8. The test specimen of claim 1, further comprising a test cooling feature structured to represent an actual cooling feature of the dual wall bonded airfoil.

9. The test specimen of claim 8, the test cooling feature including a test impingement cooling hole formed in the test spar component that is configured to represent an actual impingement cooling hole in the spar of the dual wall bonded airfoil, wherein the test impingement cooling hole is configured to impinge a cooling fluid on the test skin component.

10. The test specimen of claim 8, the test cooling feature including a test film cooling hole formed in the test skin component that is configured to represent an actual film cooling hole in the skin of the dual wall bonded airfoil, wherein said test film cooling hole is configured to discharge a cooling fluid from said test skin component.

11. The test specimen of claim 8, wherein the cooling feature includes a cooling supply channel formed in said test spar component.

12. The test specimen of claim 1, wherein said test skin component has a test skin thickness corresponding to the actual skin thickness of the skin of the dual wall bonded airfoil.

13. A method of performing life characterization of a dual wall bonded airfoil for use in a turbomachinery device, the dual wall bonded airfoil having a spar and a skin bonded to the spar, the method comprising:

forming a test specimen structured to simulate the dual wall bonded airfoil, including a test spar component, a test skin component and a test bond joint bonding said skin component to said spar component;

performing mechanical testing of the test specimen using a mechanical testing machine; and inspecting the test specimen subsequent to performing said mechanical testing.

14. The method of claim 13, further comprising heating said test specimen during said mechanical testing, said heating being configured to represent thermal conditions seen by the dual wall bonded airfoil during the operation of the turbomachinery device.

15. The method of claim 14, further comprising providing cooling air internally to said test spar component during said mechanical testing.

* * * * *